(12) United States Patent
Kliewer et al.

(10) Patent No.: US 8,029,452 B2
(45) Date of Patent: Oct. 4, 2011

(54) ARM BRACE FOR SONOGRAPHERS

(75) Inventors: Mark A. Kliewer, Madison, WI (US);
Tim Walker, Madison, WI (US);
Christopher J. Thomas, Lone Rock, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 908 days.

(21) Appl. No.: 11/844,862

(22) Filed: Aug. 24, 2007

(65) Prior Publication Data

US 2008/0051662 A1   Feb. 28, 2008

Related U.S. Application Data

(60) Provisional application No. 60/840,663, filed on Aug. 28, 2006.

(51) Int. Cl.
| | |
|---|---|
| A61G 15/00 | (2006.01) |
| A61B 19/00 | (2006.01) |
| A61B 8/00 | (2006.01) |
| A61F 5/37 | (2006.01) |
| A61F 5/00 | (2006.01) |
| A61F 13/00 | (2006.01) |
| H05G 1/02 | (2006.01) |
| H05G 1/00 | (2006.01) |
| E04B 1/19 | (2006.01) |
| F16B 7/06 | (2006.01) |
| F16B 7/10 | (2006.01) |
| F16G 11/12 | (2006.01) |
| F16C 11/06 | (2006.01) |
| F16C 11/00 | (2006.01) |

(52) U.S. Cl. .............. 602/20; 602/5; 602/12; 602/16; 602/62; 602/64; 378/193; 378/195; 378/208; 128/845; 128/869; 128/878; 128/879; 600/437; 600/446; 403/19; 403/44; 403/90; 403/112; 403/113; 403/114; 403/119; 403/122

(58) Field of Classification Search ............ 600/437, 600/439, 446; 602/5, 12, 16, 20, 21, 60–64; 128/845, 869, 878, 879; 403/19, 44–48, 403/83–85, 90, 112–114, 119, 122; 378/193, 378/195, 203–205, 208
See application file for complete search history.

(56) References Cited

U.S. PATENT DOCUMENTS

| | | | | |
|---|---|---|---|---|
| 3,490,798 A | * | 1/1970 | Spyra | 403/77 |
| 5,156,429 A | * | 10/1992 | Adams | 294/25 |
| 5,197,476 A | * | 3/1993 | Nowacki et al. | 600/439 |
| 5,379,758 A | * | 1/1995 | Snyder | 600/213 |
| 5,716,087 A | * | 2/1998 | Backich et al. | 294/55 |
| 6,324,728 B1 | * | 12/2001 | Blankenheim | 16/431 |
| 7,087,022 B2 | * | 8/2006 | Chalana et al. | 600/449 |
| 7,316,650 B1 | * | 1/2008 | Pruter | 600/437 |
| 7,517,328 B2 | * | 4/2009 | Hoffmann | 601/46 |
| 7,637,882 B2 | * | 12/2009 | Carman et al. | 602/21 |
| 7,686,740 B1 | * | 3/2010 | Chang | 482/50 |
| 2004/0084489 A1 | * | 5/2004 | Murphey et al. | 224/221 |

* cited by examiner

*Primary Examiner* — Patricia Bianco
*Assistant Examiner* — Brandon Jackson
(74) *Attorney, Agent, or Firm* — Boyle Fredrickson, S.C.

(57) ABSTRACT

A support for sonographers provides a path of force transmission from an ultrasound probe to the sonographer's upper arm bypassing the wrist, and thus reducing wrist injuries that can come from the need to tightly grip and restrain an ultrasound probe for long periods of time.

15 Claims, 2 Drawing Sheets

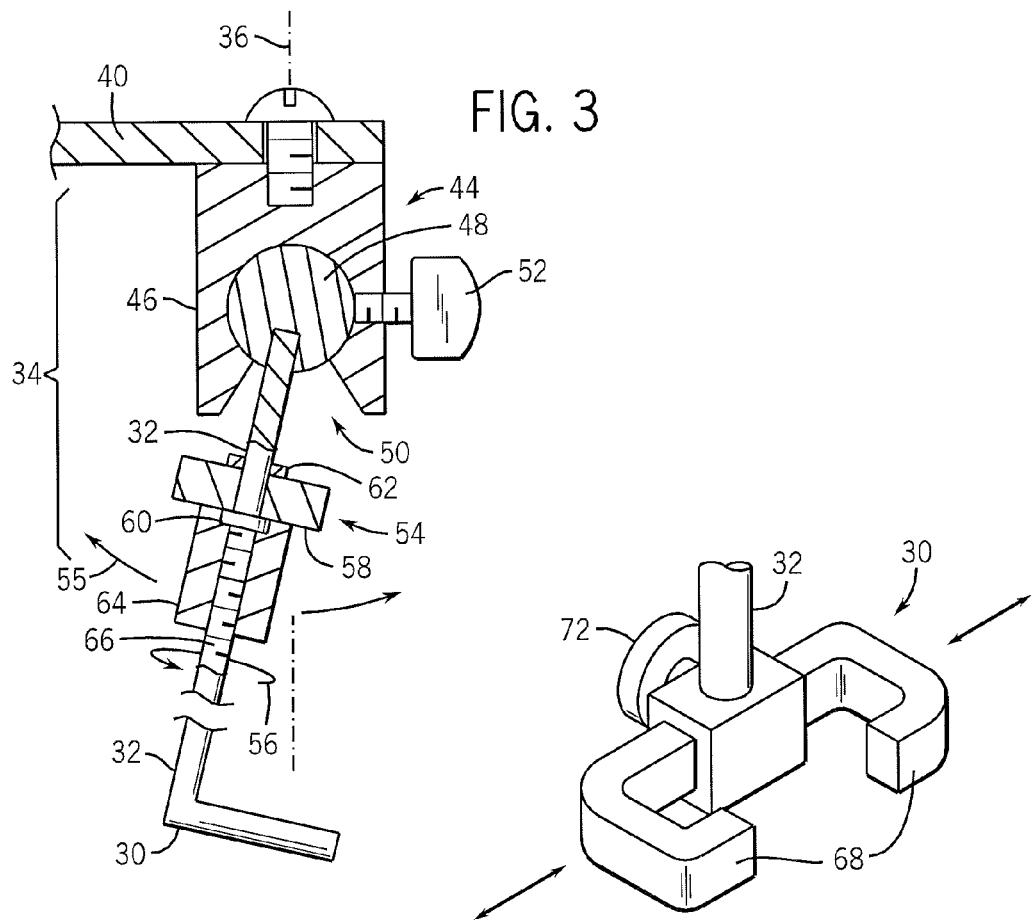
FIG. 3
FIG. 4
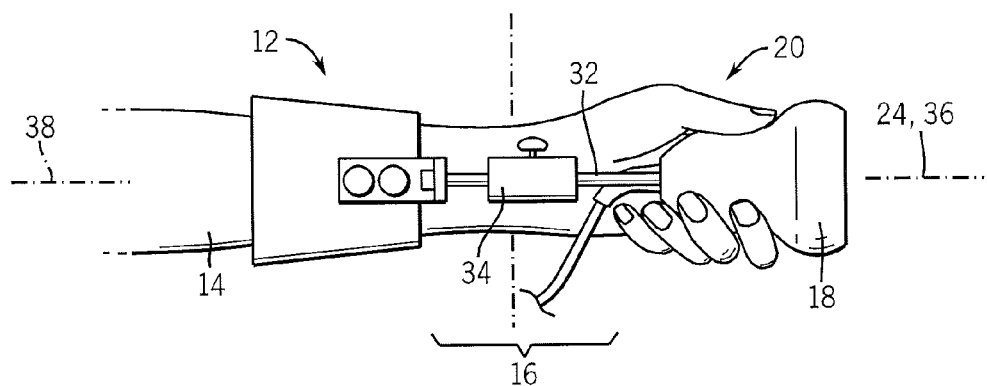
FIG. 5

ARM BRACE FOR SONOGRAPHERS

CROSS-REFERENCE TO RELATED APPLICATIONS

The present application claims the benefit of U.S. Provisional Patent Application Ser. No. 60/840,663 filed on Aug. 28, 2006.

STATEMENT REGARDING FEDERALLY SPONSORED RESEARCH OR DEVELOPMENT

BACKGROUND OF THE INVENTION

The present invention relates to apparatus for supporting ultrasound probes in medical imaging and, in particular, to a brace intended to reduce occupational injuries to sonographers.

Ultrasound medical imaging uses ultrasound sound waves to construct an image of internal body structures. During an ultrasound imaging procedure, an ultrasonic transducer (probe) is pressed against a patient to transmit ultrasound into the patient and to receive echoes that may be analyzed to produce the image. The probe is typically hand held by a sonographer to be easily manipulated to direct the ultrasound to a desired region of interest and/or to sweep the direction of the ultrasound to create a dynamic image of internal body structure.

In some obese patients, forces of up to 40 pounds of pressure are needed between the probe and the patient. Often, and especially with portable ultrasound units which are the only imaging devices available in an intensive care unit, the sonographer must assume awkward postures to reach around large or incapacitated patients. Ultrasound technologists may be required to hold and manipulate a probe against the body of a patient for long periods of time, particularly for biopsy or ablation procedures.

The probe body is normally constructed of a hard, seamless polymer shell protecting the probe electronics and allowing for easy cleaning of the probe, but making the probe difficult to grip. This problem can be exacerbated by the acoustic coupling gel normally used to increase acoustic coupling between the probe and the patient which can contaminate the surface of the probe, making it slippery. For this reason, it is known in the art to reduce the fatigue of the sonographer by placing ribs or cushioning material on the surface of the ultrasound at the probe.

In the approximately thirty years that real time ultrasonic scanning has come into prominence as a diagnostic tool, work-related injuries have become epidemic among medical sonographers. Approximately 80% of sonographers report that they have some sort of musculoskeletal complaint of the hand and wrist. Career-ending injuries due to daily stresses of sonography affect approximately 20% of the work force. The most frequent injuries are tendonitis, tenosynovitis, thoracic outlet syndrome and carpal tunnel syndrome.

SUMMARY OF THE INVENTION

The present invention provides a support that transfers force directly between the ultrasound probe and the sonographer's forearm and/or upper arm and shoulder, bypassing the sonographer's wrist. In a preferred embodiment, the ultrasound probe is flexibly connected to an arm brace, transferring forces to the arm, while allowing the sonographer to use his or her hand and wrist for minor angle and position adjustments. The brace eliminates or reduces prolonged and repeated "pinch and push" activity believed to be primarily responsible for occupational wrist injuries.

Specifically then, the present invention provides a support for a hand-held ultrasound probe having an axially extending body terminating at a transducer face emitting and receiving ultrasound. The support includes an arm brace engaging a portion of the sonographer's arm above the wrist and a coupling element attached to the arm brace and extending below the sonographer's wrist to attach to an ultrasound probe held by the sonographer. The arm brace and coupling operate so that a portion of the force on the probe, when the probe is pressed against the patient by the sonographer, is communicated through the coupling directly to the sonographer's arm, bypassing the sonographer's wrists.

Thus, it is an object of at least one embodiment of the invention to transfer at least a portion of the force required for medical ultrasound imaging away from the sonographer's wrist area to the more robust structure of the sonographer's arm.

The coupling may allow angulation of the axis of the probe.

It is therefore an object of at least one embodiment of the invention to let the sonographer manipulate the angle of the probe, without feeling the full force exerted on the probe by the patient tissue against his or her hand.

The coupling may be a ball joint.

It is thus another object of at least one embodiment of the invention to provide a coupling that allows for low friction angulation and/or rotation while fully transmitting axial forces.

The coupling may include a lock locking axial realignment of the coupling.

Thus, it is an object of at least one embodiment of the invention to allow the sonographer to alternatively angulate the probe and lock the probe into position, eliminating the need to apply continuous gripping force on the ultrasound probe for long procedures.

The coupling may allow rotation of the axis of the probe.

Thus, it is an object of at least one embodiment of the invention to allow freedom of rotation of the probe while eliminating the need to tightly grip the probe against axially-applied forces or angulation of the probe.

The arm brace may attach to a forearm of the sonographer.

Thus, it is an object of at least one embodiment of the invention to provide a relatively large area of contact behind the wrist that may receive forces without unduly interfering with the freedom of the sonographer's arm. It is another object of at least one embodiment of the invention to provide a brace point local to the sonographer's wrist.

The arm brace may be a helix sized to wrap around the forearm.

Thus, it is an object of at least one embodiment of the invention to provide a simple brace that resists forces in multiple directions.

The arm brace may include at least one strap cinchable about the forearm.

Thus, it is another object of at least one embodiment of the invention to provide a brace that may be readily adapted to a wide variety of sonographers.

The coupling may provide constrained angulation about an axis substantially perpendicular to an axis of the sonographer's forearm.

It is thus an object of at least one embodiment of the invention to allow the sonographer to easily apply and control forces perpendicular to the axis of the forearm, for example, downward or upward.

Alternatively, the coupling may provide constrained angulation along an axis substantially aligned with an axis of a sonographer's forearm.

Thus, it is another object of at least one embodiment of the invention to allow support for a probe used in a thrusting orientation.

The coupling may provide adjustments for repositioning the ultrasound probe with respect to the sonographer's hand.

Thus, it is an object of at least one embodiment of the invention to allow the ultrasound probe to be comfortably gripped by the sonographer for a variety of different sonographer arm sizes and procedures.

The arm brace may allow free movement of the sonographer's wrist.

Thus, it is an object of at least one embodiment of the invention not to unduly hamper the sonographer's freedom of motion.

The coupling may provide for a releasable attachment to the probe.

Thus, it is another object of at least one embodiment of the invention to provide a support that may be used with a variety of different ultrasound probes.

These particular objects and advantages may apply to only some embodiments falling within the claims and thus do not define the scope of the invention.

BRIEF DESCRIPTION OF THE DRAWINGS

FIG. 3 is a simplified cross-sectional view through the coupling of FIGS. 1 and 2 which allows angulation, rotation and extension of the position of the ultrasound probe and which permits locking of angulation;

FIG. 4 is a detailed perspective view of a releasable grip for holding the coupling to the probe; and FIG. 5 is a simplified, side elevational view of a second embodiment of the invention for orientation of the probe with its axis aligned with the axis of the forearm.

DETAILED DESCRIPTION OF THE PREFERRED EMBODIMENT

Figure 1:
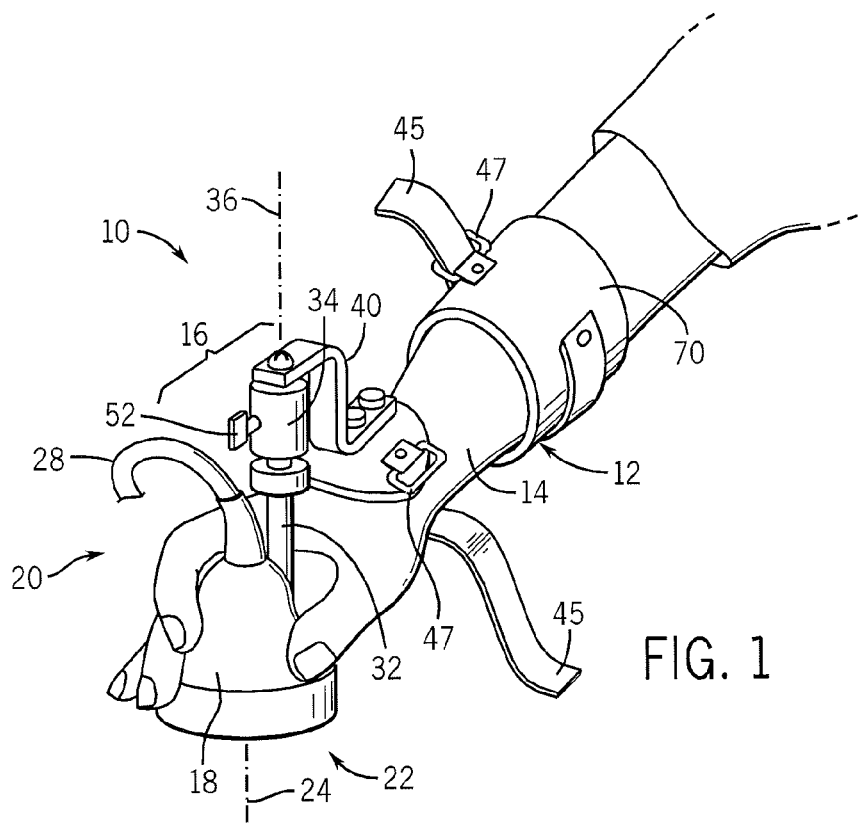
FIG. 1 is a perspective view of the ultrasound probe support of the present invention having an arm brace fitted to a sonographer's arm and showing a coupling communicating with an ultrasound probe.

Referring now to FIG. 1, an ultrasound probe support 10 of the present invention may include generally an arm brace 12 for attachment to the forearm 14 of a sonographer. A distal end of the arm brace 12 supports a coupling 16 that communicates between the arm brace 12 and an ultrasound probe 18 that may be held by the sonographer's hand 20.

Figure 2:
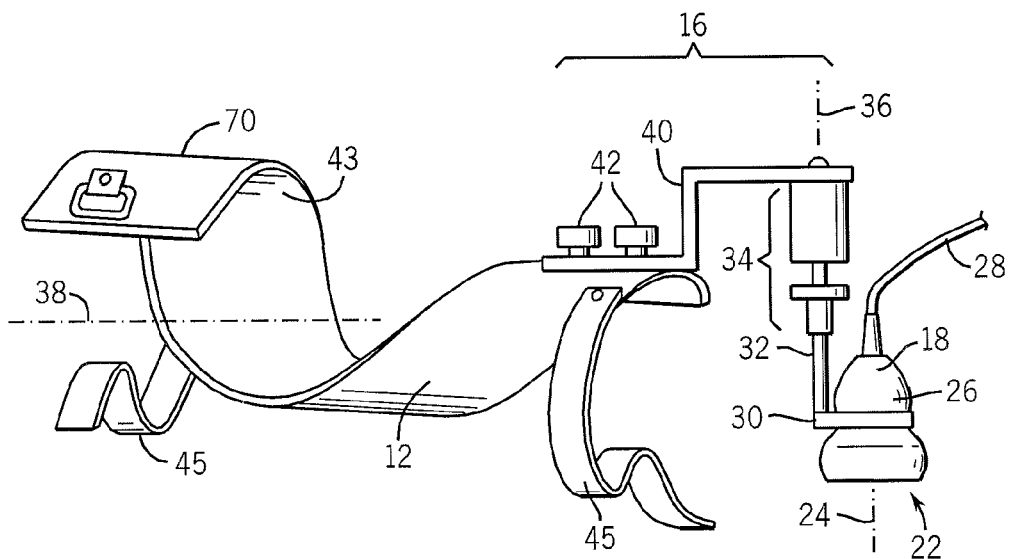
FIG. 2 is a side elevational view of the support of FIG. 1 showing a perpendicular relationship between the ultrasound probe axis and the axis of the forearm.

Referring now also to FIG. 2, the ultrasound probe 18 will generally have an axially extending probe body 26 terminating at one end at a probe face 22 from which ultrasonic signals are emitted and echo signals are received along an ultrasound axis 24. A signal cord 28 may extend from the opposite end of the probe body 26, the signal cord attaching the ultrasound probe 18 to an ultrasound machine (not shown) which processes received ultrasonic data to produce images as is understood in the art.

The ultrasound probe 18 is connected to one end of the coupling 16 by means of a grip 30 removably connected to the body 26 of the ultrasound probe 18. The grip 30 attaches the ultrasound probe 18 to a shaft 32 generally parallel to the axis of the ultrasound probe 18, and the shaft 32 in turn is received by a joint 34. As will be described in greater detail, a joint 34 allows for constrained movement of the probe 18 under guidance of the sonographer's hand about a pivot centerline 36.

In a first embodiment, the joint 34 is placed above the probe 18 to provide a pivot centerline 36 generally perpendicular to the axis of the sonographer's forearm 14. The joint 34 is removed from the vicinity of the sonographer's hand to provide adequate angular excursion of the shaft 32 through small angles that can be stabilized by the sonographer's hand without excessive force and yet to position the probe 18 at the sonographer's hand when the sonographer's hand is in a relaxed position with the wrist generally straight.

The joint 34 may be attached to a bracket 40 providing the appropriate displacement of the joint 34 above the normal resting position of the sonographer's hand. The bracket 40 attaches to a distal end of the arm brace 12 by means of finger nuts 42 that may be loosened to allow adjustment of the bracket 40 along the forearm axis 38 by means of threaded studs passing through slots in the bracket 40 (not shown). In this way, the location of the probe 18, in a neutral position with the ultrasound axis 24 aligned with pivot centerline 36, may be readily adjusted for different sonographers. The finger nuts 42 also allow removal of the coupling 16 for cleaning or to fit with different arm braces 12.

Referring now to FIG. 3, joint 34 consists of two principal elements. The first element is a ball joint 44 having a spherical socket 46, and a ball 48 pivoting within the spherical socket 46. The socket 46, simplified for clarity, is attached to the underside of bracket 40 and provides a downward opening 50 allowing shaft 32 to attach to the ball 48 and to move in limited angulation 55 of shaft 32 about the pivot centerline 36 with rotation of the ball 48.

A locking screw 52 may pass through a threaded hole in the socket 46 to abut a surface of the ball 48 when the locking screw 52 is tightened. The locking screw 52 thus allows a clamping of the ball 48 at a particular angle when the sonographer tightens the locking screw 52 with the sonographer's other hand. Alternatively, electrical, hydraulic or pneumatic locks allowing remote activation through foot pedals, voice or switches accessible to the sonographer while holding the ultrasound probe 18 may be readily provided, as will be understood to those of ordinary skill in the art.

A second portion of the joint 34 provides a swivel coupling 54 placed along the shaft 32 that allows rotation 56 of the shaft 32 about its axis as well as extension of the shaft 32. In particular, the swivel coupling 54 includes a rotation ring 58 attached to an upper portion of the shaft 32 connecting to the ball 48. The rotation ring 58 may rotate about the shaft 32 but may be constrained against axial motion along the shaft 32 by a head 60 formed in the lower portion of the shaft 32 on one side of the rotation ring 58, and a snap ring 62 on the other side of the rotation ring 58.

A sleeve 64 extends downward from the rotation ring 58 to rotate therewith and has an internally threaded bore which may receive a threaded upper end 66 of a lower portion of the shaft 32. Rotation of the rotation ring 58 allows for rotation 56 of the probe 18 held by the grip 30 even when the ball 48 is locked. Alternatively, when the grip 30 is stabilized against rotation, rotation of the rotation ring 58 allows adjustment of the extension of the shaft 32 and thus the height of the grip 30.

Referring now to FIG. 4, the grip 30 may provide for a clamp having opposed clamp fingers 68 that may be adjusted in separation by an adjustment knob 72 or the like, for example, driving a pinion gear engaging opposed racks (not shown) attached to the opposite clamp fingers 68. In this way, a variety of different ultrasound probes 18 may be securely gripped and held by the grip 30.

Referring again to FIG. 1, it will thus be understood that during an ultrasound medical procedure, the sonographer may press downward on the ultrasound probe 18 using the muscles of the forearm 14 without significant force on the sonographer's wrist or the need to tightly grip the ultrasound probe 18. Movement of the forearm 14 may be used to position the effective pivot point of the ultrasound probe 18 (e.g., the center of the ball 48) to direct the force as desired. The sonographer's hand may be used to make minor adjustments in the angulation and rotation without confronting the full force acting on the probe 18, the latter which is reduced by the sine of the divergence of ultrasound axis 24 and pivot centerline 36 and which is, for small angles, many times lower than the actual force. Rotation of the probe 18 may be obtained by hand independent of the axial force.

When a particular angle must be sustained for a long period of time, the joint 34 may be locked with respect to angulation through use of the locking screw 52 or other locking mechanisms described above. At this time, the sonographer's wrist is essentially free from stress, with the major forces being undertaken by the sonographer's forearm 14.

Referring now to FIG. 5, it will be understood that the principles of the present invention may be readily modified for other ultrasonic procedures, for example, one in which the ultrasound axis 24 of the ultrasound probe 18 is generally aligned with the forearm axis 38 of the sonographer's forearm. In this case, the joint 34 is placed approximately aligned with the wrist of the sonographer along the forearm axis 38 to direct the pivot centerline 36 along the forearm axis 38.

Referring again to FIG. 1, the arm brace 12 may provide for a helical band 70 of substantially rigid material, for example, a thermoplastic or fiber composite material, providing a band wrapping about the forearm of the standard adult. The helical band 70 may decrease in diameter as one moves from the proximal to the distal end of the arm brace 12, conforming to the taper of a person's forearm, and providing improved resistance to forces along the forearm axis 38. An inner surface of the band may include a replaceable cushion 43 whose thickness may be changed to accommodate different sonographers. Different helical bands 70 may also be provided to fit different individuals.

Straps 45 (shown loosened) may be provided at distal and proximate ends of the helical band 70 of the arm brace 12 to pass circumferentially about the sonographer's forearm 14 to be received by corresponding loops 47 and cinched, for example, using hook and loop-type fasteners attached on opposite surfaces of the straps 45, as is understood in the art. The axial progression of the helix of the arm brace 12 and the radial passage of the straps 45 allow the bands to directly contact the skin of the forearm 14 holding the helical band 70 of the arm brace 12 snugly against the forearm 14 for a variety of different sonographers. Other arm brace designs, for example those using opposed axially extending shells and the like, are also contemplated.

It will be understood that the coupling 16, as generally spans the sonographer's wrist, is intended to provide a path of transmission of at least a portion of the forces on the probe 18 directly to the forearm 14 or the like, bypassing the sonographer's wrist and eliminating the need for tight gripping by the sonographer. It will be apparent from this description that the coupling need not be a ball joint but that alternative couplings, including those generally providing a malleable link or a spring, nevertheless providing for a path of force transmission, are also contemplated.

When a mechanical joint 34 is used, it may further provide for a spring or other mechanical centering so as to shield the user against the need to brace the probe against strong forces of angulation. As an alternative to the grip 30 described herein, manufacturers may provide for standard sockets or the like incorporated into the bodies of the ultrasound probes that may attach to corresponding elements on the end of the shaft 32.

It is specifically intended that the present invention not be limited to the embodiments and illustrations contained herein, but include modified forms of those embodiments including portions of the embodiments and combinations of elements of different embodiments as come within the scope of the following claims.

We claim:

1. A support for a hand-held ultrasound probe having an axially extending body terminating at a transducer face emitting and receiving ultrasound along an axis, the support comprising:
    an arm brace adapted to engage a portion of a sonographer's arm above the wrist;
    a coupling element attached to the arm brace distal to the sonographer's wrist at a location removed from a palm of a hand of the wrist of the sonographer when the arm brace engages the portion of the sonographer's arm, the coupling element including a pivot;
    an ultrasound probe attached to the coupling element so that the ultrasound probe is positionable to be grasped in the palm of the hand of the sonographer to manipulate the pivot to change an angle of the axis of the probe with respect to an axis of the sonographer's arm; and
    whereby at least a portion of a force on the probe when the probe is pressed against a patient by the sonographer is communicated through the coupling to the sonographer's arm while bypassing the sonographer's wrist.

2. The support of claim 1 wherein the coupling allows angulation of the axis of the probe.

3. The support of claim 2 wherein the coupling is a ball joint.

4. The support of claim 2 wherein the coupling includes a lock, locking axial realignment of the probe.

5. The support of claim 1 wherein the arm brace attaches to a forearm extending from the wrist of the sonographer.

6. The support of claim 5 wherein the arm brace is a helix sized to wrap around the forearm.

7. The support of claim 5 wherein including at least one strap cinchable about the forearm.

8. The support of claim 1 wherein the coupling allows orientation of the axis of the probe.

9. The support of claim 1 wherein the coupling provides constrained angulation about an axis substantially perpendicular to an axis of a forearm extending from the wrist of the sonographer.

10. The support of claim 1 wherein the coupling provides constrained angulation about an axis substantially aligned with an axis of a forearm extending from the wrist of the sonographer.

11. The support of claim 1 wherein the coupling provides a length adjustment.

12. The support of claim 1 wherein the coupling provides a releasable attachment to the probe.

13. The support of claim 1 wherein the arm brace allows free movement of the sonographer's wrist.

14. A kit for a brace for a hand-held ultrasound probe having an axially extending body terminating at a transducer face emitting and receiving ultrasound along an axis, the support comprising:

a set of arm braces adapted to engage a portion of a sonographer's arm above the wrist, the arm braces sized to fit different sonographers;

a coupling element attachable to the each given arm brace distal to the sonographer's wrist at a location removed from a palm of a hand extending from the wrist of the sonographer when the arm brace engages the portion of the sonographer's arm, the coupling element including a pivot;

an ultrasound probe attached to the coupling element so that the ultrasound probe is positionable to be grasped in the palm of the hand of the sonographer to manipulate the pivot to change an angle of the axis of the probe with respect to an axis of the sonographer's arm; and whereby at least a portion of a force on the probe when the probe is pressed against a patient by the sonographer is communicated through the coupling to the sonographer's arm while bypassing the sonographer's wrist.

15. The kit of claim 14 wherein the set of arm braces include at least one stiff shell interfitting with different cushions to fit different sonographers.

* * * * *